United States Patent
Sjostrom et al.

(10) Patent No.: US 6,736,883 B2
(45) Date of Patent: May 18, 2004

(54) PARTICULATE SEPARATION SYSTEM FOR MERCURY ANALYSIS

(75) Inventors: Sharon Sjostrom, Denver, CO (US); Timothy Ebner, Westminster, CO (US); Richard Slye, Denver, CO (US)

(73) Assignee: Apogee Scientific, Inc., Englewood, CO (US)

( * ) Notice: Subject to any disclaimer, the term of this patent is extended or adjusted under 35 U.S.C. 154(b) by 0 days.

(21) Appl. No.: 10/307,755

(22) Filed: Dec. 2, 2002

(65) Prior Publication Data

US 2003/0110950 A1 Jun. 19, 2003

Related U.S. Application Data

(60) Provisional application No. 60/340,799, filed on Dec. 14, 2001.

(51) Int. Cl.[7] ............................................... B01D 46/46
(52) U.S. Cl. ..................... 96/112; 55/523; 55/DIG. 34; 73/863.23; 95/18; 95/134; 96/413; 422/88; 436/81
(58) Field of Search ............................ 95/14, 18, 134; 96/112, 413; 422/88; 436/81; 55/523, DIG. 34; 73/863.23, 863.24

(56) References Cited

U.S. PATENT DOCUMENTS

| | | | |
|---|---|---|---|
| 4,161,883 A | | 7/1979 | Laird et al. ............... 73/863.24 |
| 4,186,100 A | | 1/1980 | Mott ........................... 210/496 |
| 4,379,412 A | | 4/1983 | Wood ....................... 73/863.24 |
| 4,419,107 A | | 12/1983 | Roydhouse ..................... 95/59 |
| 5,403,365 A | * | 4/1995 | Merriam et al. .............. 44/621 |
| 5,413,001 A | * | 5/1995 | Jarolics .................... 73/863.83 |
| 5,482,538 A | * | 1/1996 | Becker et al. .................. 95/12 |
| 5,505,825 A | * | 4/1996 | Gold et al. .................... 95/126 |
| 5,854,173 A | * | 12/1998 | Chang et al. ................ 502/417 |
| 5,917,066 A | | 6/1999 | Eisenmann et al. ........... 55/502 |
| 5,948,143 A | * | 9/1999 | Sjostrom et al. .............. 95/134 |
| 6,068,685 A | * | 5/2000 | Lorimer et al. ............... 96/112 |
| 6,176,896 B1 | * | 1/2001 | Dementhon et al. .......... 95/14 |
| 6,475,802 B2 | * | 11/2002 | Schaedlich et al. .......... 436/81 |
| 6,589,795 B2 | * | 7/2003 | Tyson et al. .................. 436/81 |

FOREIGN PATENT DOCUMENTS

JP          1-270925     * 10/1989        95/14

* cited by examiner

*Primary Examiner*—Richard L. Chiesa
(74) *Attorney, Agent, or Firm*—Dorr, Carson, Sloan, Birney & Kramer, P.C.

(57) ABSTRACT

A particulate separation system for accurate measurement of vapor-phase mercury in a flue gas stream uses an inertial gas sampling filter in which the skin temperature of the filter element is controlled to allow vapor-phase mercury measurements while minimizing measurement artifacts caused by: (1) mercury thermally desorbing off particulates into the gas stream; and (2) mercury being removed from the vapor phase by collection on particulate matter at the gas/particle separation interface.

20 Claims, 2 Drawing Sheets

US 6,736,883 B2

PARTICULATE SEPARATION SYSTEM FOR MERCURY ANALYSIS

RELATED APPLICATION

The present application is based on, and claims priority to U.S. Provisional Patent Application Ser. No. 60/340,799, filed on Dec. 14, 2001.

BACKGROUND OF THE INVENTION

1. Field of the Invention

The present invention relates generally to the field of systems for measuring mercury in flue gas streams. More specifically, the present invention discloses a particulate separation system for mercury analysis in flue gas streams.

2. Statement of the Problem

Several approaches are currently employed to measure vapor-phase mercury in flue gas streams containing particulate matter. However, these techniques introduce sampling artifacts that are not adequately addressed by the current methods. Many particulates present in flue gas streams have an affinity for mercury and may remove vapor-phase mercury from the gas stream or convert mercury from one vapor-phase species to another. For example, fly ash particles have been shown to both remove mercury and oxidize mercury. Many current measurement techniques use a filter to separate the particulate matter from the gas stream. However, if the particulate matter separated from the gas stream is not inert, the vapor-phase mercury measured downstream from the filter will not accurately represent the mercury upstream from the filter.

An example of an inertial filter in the conditioning assembly for continuous stack monitoring was disclosed by the Bendix Corporation in U.S. Pat. No. 4,161,883 (Laird et al.). Mott Metallurgical Corporation also offers an inertial gas sampling filter similar to the Bendix inertial filter. The Mott filter effectively separates the majority of the particulate matter from the gas stream and filters the remaining particulate matter. If the gas stream contains particulates with a low affinity for mercury and a large fraction of particles that can be efficiently separated by means of an inertial filter (i.e., particles having a relatively large aerodynamic diameter), the Mott system should work well to provide a particulate-free gas stream for measurement of vapor-phase mercury without altering the species of mercury (i.e., particulate, oxidized vapor, or elemental vapor). However, for gas streams containing particles with an affinity for mercury or gas streams with a large fraction of small particles, the Mott system can introduce significant sampling artifacts from the thin layer of particulate matter collected on the filter surface.

3. Solution to the Problem

The present invention is a modified inertial filter that addresses the shortcomings associated with the prior art by including a heater and temperature controller that maintain the inertial filter within a predetermined temperature range. This enables accurate measurement of vapor-phase mercury without biasing the measurement due to desorption of particulate-phase mercury or absorption of mercury vapor onto fine particles that have an affinity for mercury.

SUMMARY OF THE INVENTION

This invention provides a particulate separation system for accurate measurement of vapor-phase mercury in a flue gas stream. The process uses an inertial gas sampling filter in which the skin temperature of the filter element is controlled to allow vapor-phase mercury measurements while minimizing measurement artifacts caused by: (1) mercury thermally desorbing off particulates into the gas stream; and (2) mercury being removed from the vapor phase by collection on particulate matter at the gas/particle separation interface.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
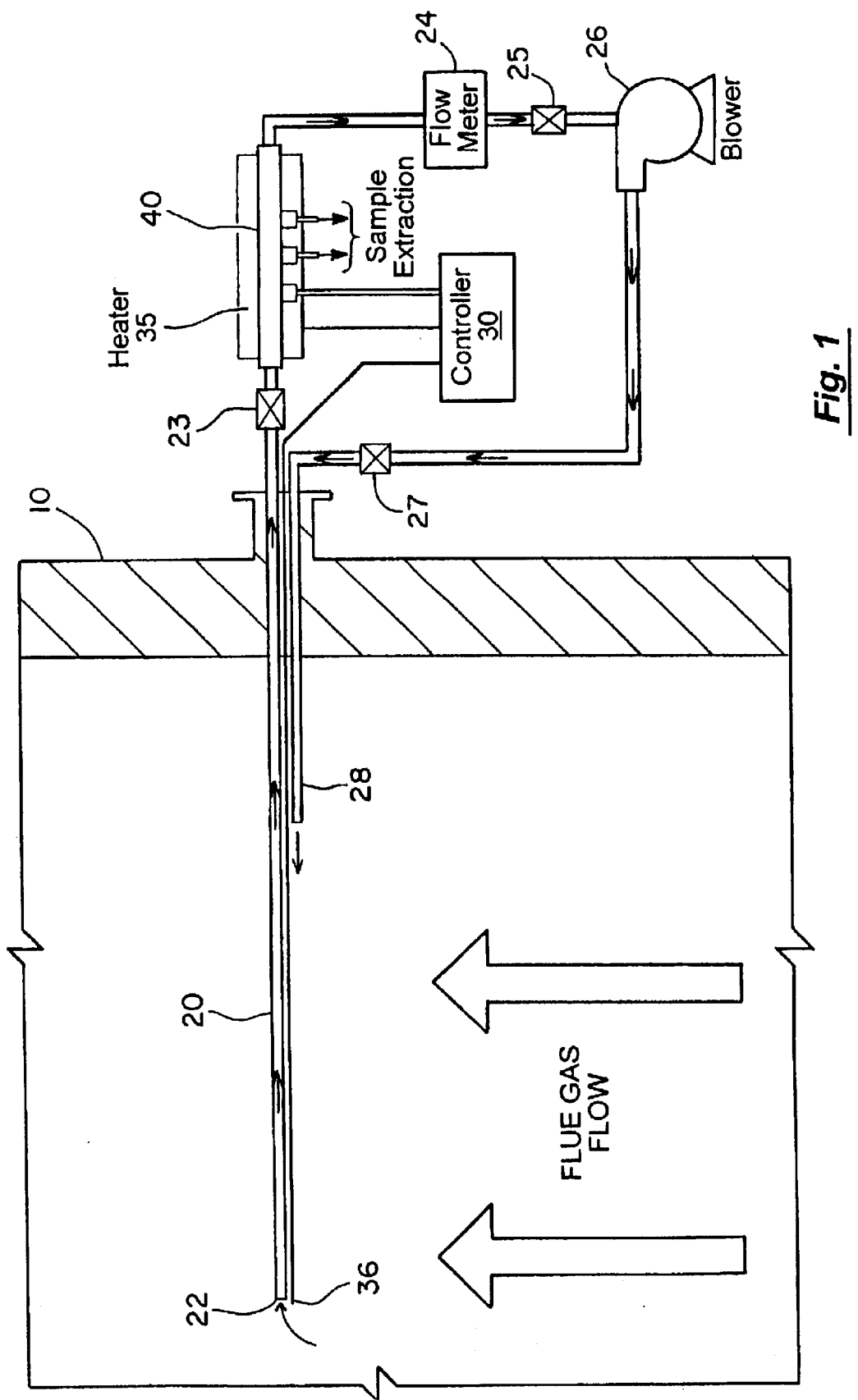
FIG. 1 is a diagram of an installation of the present invention to filter particulates from flue gas samples.

Turning to FIG. 1, a diagram is provided showing a typical installation of the present invention. The portion of FIG. 1 to the left of the duct wall 10 represents the exhaust stack for the flue gases to be sampled. An inlet probe 20 extends through the duct wall 10 into the flue gases. Flue gases are drawn through the distal opening 22 of the inlet probe 20 by a blower 26 and pass through an inertial gas separation filter 40, at which point gas samples can be withdrawn for analysis. The flow meter 24 measures the flow rate of gas withdrawn from the exhaust stack. This flow rate can be adjusted by means of a flow control valve 25. The remaining gas exiting the blower 26 returns to the exhaust stack via an exhaust probe 28 that extends through the duct wall 10. Alternatively, an eductor pump can be used in place of a blower 26 to draw gas from the exhaust stack. The system is also equipped with an inlet isolation valve 23 and an outlet isolation valve 27 so that the inertial gas separation filter 40, flow meter 24 and blower 26 can be isolated from the exhaust stack for service, cleaning, or replacement. If desired, the position of the opening 22 at the distal end of the inlet probe 20 can be adjusted to sample flue gases at a variety of points across the exhaust stack. For example, this can be accomplished by constructing the inlet probe from a series of tubular segments that be attached together with connectors to form a desired length. A telescoping series of tubular segments could also be substitute for this purpose.

Figure 2:
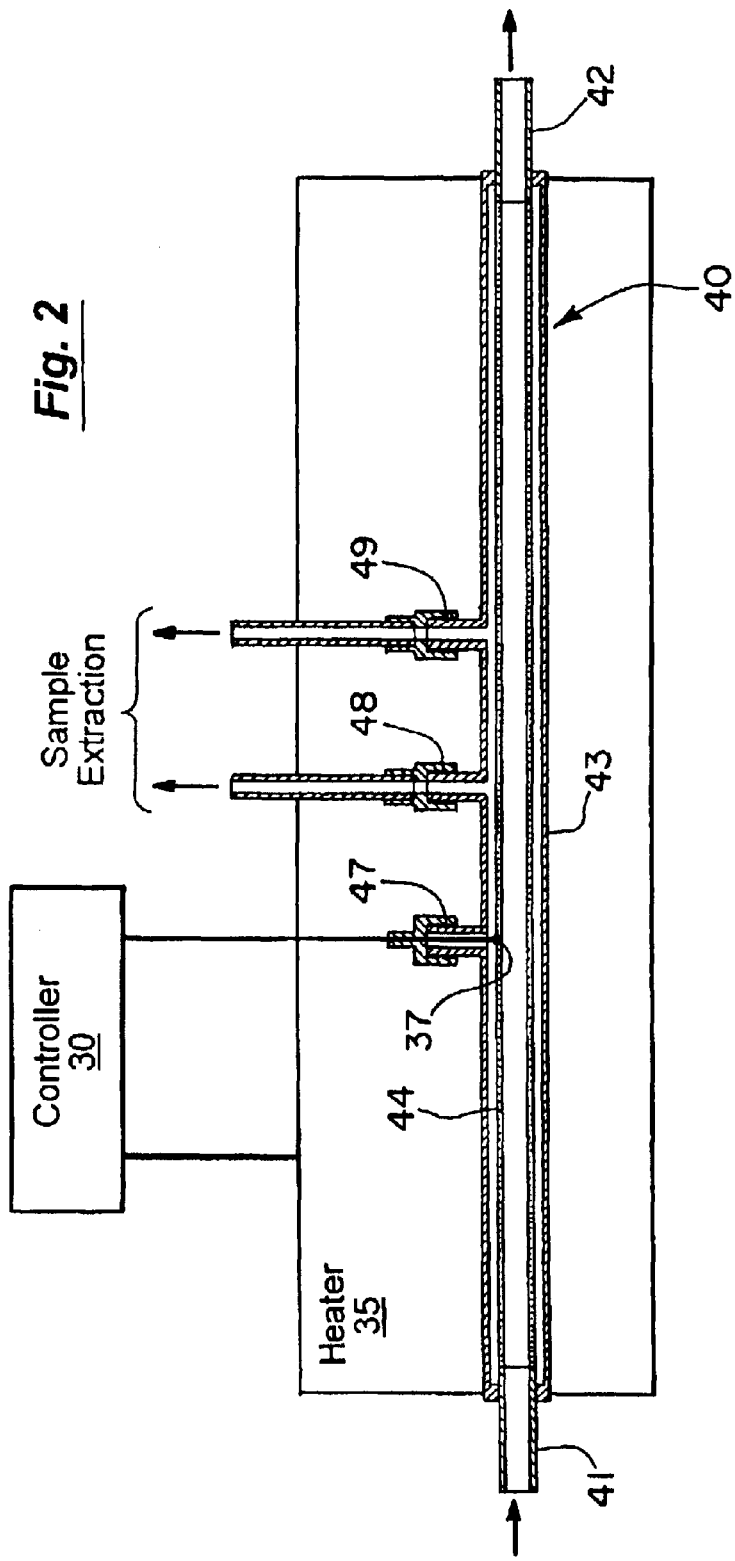
FIG. 2 is a side cross-sectional view of the inertial gas separation filter 40 and heater assembly 35.
Figure 3:
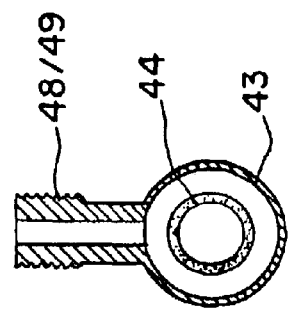
FIG. 3 is a cross-sectional view of the inertial gas separation filter 40 taken along the plane of one of the sample extraction ports 48, 49 in FIG. 2.

FIG. 2 is a side cross-sectional view of the inertial gas separation filter 40 and heater assembly 35. FIG. 3 is an orthogonal cross-sectional view of the inertial gas separation filter 40. The inertial gas separation filter 40 includes an inlet tube 41 leading from the inlet probe 20 and an outlet tube 42 that connects to the flow meter 24 and blower 26. Exhaust gases flow from the inlet tube 41 through an inner sintered tube 44 that is surrounded by an outer tube 43. The outer tube 43 is made of stainless steel tubing. The inner tube 44 serves as a filter element and is made of a sintered porous metal tube. The vast majority of the particles entrained in the gas stream are prevented from depositing on or penetrating into the porous sintered tube 44 by the high-speed in-line gas flow and particle inertia. The finer particles form a permeable subsurface on the wall of the sintered tube 44. The sintered tube 44 has an average pore size selected to prevent passage of particulates greater than a predetermined minimal size. The exhaust gases passing through the sintered tube 44 are contained within the outer tube 43 and can be withdrawn for analysis via one or more sample extraction ports 48, 49.

The present system is also equipped with at least two temperature sensors, e.g., thermocouples 36 and 37. The first temperature sensor 36 is used to measure the temperature of flue gases in the exhaust stack adjacent to the inlet probe 20. For example, the first temperature sensor 36 can be mounted to a thin support rod extending through the duct wall 10 to a position upstream from, but adjacent to the distal opening 22 of the inlet probe 20 to maximize its thermal isolation. Alternatively, the first temperature sensor 36 could be attached to the inlet probe 20. The second temperature sensor 37 measures the temperature of the inner sintered tube 44, as illustrated in FIG. 2, via a thermocouple port 47 in the outer tube 43.

Both temperature sensors 36, 37 are monitored by a controller 30 (e.g., a computer processor or PID controller) to determine the difference in temperatures between the gas stream entering the inlet probe 20 and the sintered tube 44. A heater 35 regulated by the controller 30 maintains the temperature of the sintered tube within a small predetermined range of the temperature of the gas stream entering the inlet probe 20. For example, the heater 35 could be an enclosure with an electrical heating element surrounding the outer tube 43 and the inner sintered tube 44.

During operation of the filter 40, the temperature of the sintered tube 44 is maintained by the heater 35 at a temperature such that the mercury adsorption capacity of the particulate matter collecting on the sintered tube 44 removes only minimal additional mercury from the gas stream. However, to prevent mercury from desorbing off particles that have already be separated from the gas flow or desorbing off particles in the gas flow, minimal changes in the temperature of the gas flow are allowable. In other words, the filter 40 is maintained at a temperature high enough to significantly lower the mercury adsorption capacity of any particulates collecting on the filter element 44, while minimizing any temperature increase in the gas stream which could cause mercury to desorb from the particulate matter in the gas stream. This process efficiently separates particulate matter from a gas stream with minimal change to the speciation of the mercury (i.e., particulate mercury, oxidized vapor-phase mercury, or elemental vapor-phase mercury). The particulate-free gas can then be delivered to a mercury analyzer or manual mercury measurement system.

The fabrication process for the filter 40 can also include sufficiently preheating the outer tube 43 versus the inner sintered tube 44 to compensate for the high thermal differential that can exist between the filter element 44 and the outer tube 43. This fabrication process helps to prevent fractures or cracking of the sintered tube 44 due to thermal stresses.

The above disclosure sets forth a number of embodiments of the present invention. Other arrangements or embodiments, not precisely set forth, could be practiced under the teachings of the present invention and as set forth in the following claims.

We claim:

1. A gas sampling filter for use in a system for measurement of vapor-phase mercury in a flue gas stream, said filter comprising:
    a filter element to separate particulates from the gas being sampled;
    a heater heating the filter element;
    a first temperature sensor measuring the temperature of the flue gas stream;
    a second temperature sensor measuring the temperature of the filter element; and
    a controller regulating the heater to minimize the difference between the temperature of the flue gas stream measured by the first temperature sensor and the temperature of the filter element measured by the second temperature sensor.

2. The gas sampling filter of claim 1 wherein the filter element comprises a sintered tube having a wall with sufficient porosity to allow a sample of the flue gas stream to be drawn through the wall of the sintered tube, and having an average pore size selected to separate particulates from the gas being sampled.

3. The gas sampling filter of claim 2 further comprising an outer tube surrounding the sintered tube, wherein flue gas passes through the sintered tube and a sample of flue gas is drawn through the wall of the sintered tube into the outer tube.

4. A gas sampling filter for use in a system for measurement of vapor-phase mercury in a flue gas stream, said filter comprising:
    a sintered tube within an outer tube having an inlet and outlet for passing at least a portion of the flue gas stream, and having a wall with sufficient porosity to allow a sample of the flue gas stream to be drawn through the wall of the sintered tube, but having an average pore size selected to separate particulates from the flue gas being sampled;
    a heater heating the sintered tube;
    a first temperature sensor measuring the temperature of the flue gas stream;
    a second temperature sensor measuring the temperature of the sintered tube; and
    a controller regulating the heater to minimize the difference between the temperature of the flue gas stream measured by the first temperature sensor and the temperature of the sintered tube measured by the second temperature sensor.

5. The gas sampling filter of claim 4 further comprising the outer tube surrounding the sintered tube, wherein a sample of flue gas is drawn through the wall of the sintered tube into the outer tube.

6. The gas sampling filter of claim 5 wherein the heater surrounds the sintered tube and the outer tube.

7. A system for sampling vapor-phase mercury in a flue gas stream flowing through a duct, said system comprising:
    an inlet probe to withdraw flue gas from the duct;
    a gas sampling filter having a sintered tube receiving the flue gas withdrawn through the inlet probe, said sintered tube having a wall with sufficient porosity to allow a sample of the flue gas to be drawn through the wall of the sintered tube, but having an average pore size selected to separate particulates from the flue gas being sampled;
    a heater heating the sintered tube;
    a first temperature sensor measuring the temperature of the flue gas at the inlet probe;
    a second temperature sensor measuring the temperature of the sintered tube; and
    a controller regulating the heater to minimize the difference between the temperature of the flue gas measured by the first temperature sensor and the temperature of the sintered tube measured by the second temperature sensor; and
    a blower drawing flue gas from the duct through the inlet probe and gas sampling filter.

8. The system of claim 7 further comprising a flow meter measuring the flow of flue gas through the gas sampling filter.

9. The system of claim 7 further comprising an outer tube surrounding the sintered tube, wherein a sample of flue gas is drawn through the wall of the sintered tube into the outer tube.

10. The system of claim 7 further comprising a flow control valve regulating the flow of flue gas through the gas sampling filter.

11. The system of claim 7 wherein the inlet probe further comprises a distal opening that can be adjustably positioned within the duct.

12. The system of claim 7 further comprising a support rod supporting the first temperature sensor within the duct adjacent to the inlet probe.

13. A gas sampling filter for use in a system for measurement of vapor-phase mercury in a flue gas stream, said filter comprising:

a sintered tube within an outer tube having an inlet and outlet for passing at least a portion of the flue gas stream, and having a wall with sufficient porosity to allow a sample of the flue gas stream to be drawn through the wall of the sintered tube, but having an average pore size selected to separate particulates from the flue gas being sampled;

a heater heating the sintered tube; and a controller regulating the heater to maintain a selected minimum temperature of the sintered tube to lower the mercury adsorption capacity of particulates collected on the filter, and minimizing any temperature increase in the flue gas stream through the filter to prevent desorption of mercury from particulates in the flue gas stream.

14. The gas sampling filter of claim 13 further comprising the outer tube surrounding the sintered tube, wherein a sample of flue gas is drawn through the wall of the sintered tube into the outer tube.

15. The gas sampling filter of claim 14 wherein the heater surrounds the sintered tube and the outer tube.

16. A system for sampling vapor-phase mercury in a flue gas stream flowing through a duct, said system comprising:

an inlet probe to withdraw flue gas from the duct;

a gas sampling filter having a sintered tube receiving the flue gas withdrawn through the inlet probe, said sintered tube having a wall with sufficient porosity to allow a sample of the flue gas to be drawn through the wall of the sintered tube, but having an average pore size selected to separate particulates from the flue gas being sampled;

a heater heating the sintered tube; and a controller regulating the heater to maintain a selected minimum temperature of the sintered tube to lower the mercury adsorption capacity of particulates collected on the filter, and minimizing any temperature increase in the flue gas stream through the filter to prevent desorption of mercury from particulates in the flue gas stream; and a blower drawing flue gas from the duct through the inlet probe and gas sampling filter.

17. The system of claim 16 further comprising a flow meter measuring the flow of flue gas through the gas sampling filter.

18. The system of claim 16 further comprising an outer tube surrounding the sintered tube, wherein a sample of flue gas is drawn through the wall of the sintered tube into the outer tube.

19. The system of claim 16 further comprising a flow control valve regulating the flow of flue gas through the gas sampling filter.

20. The system of claim 16 wherein the inlet probe further comprises a distal opening that can be adjustably positioned within the duct.

* * * * *